US009072770B2

(12) United States Patent
Lin et al.

(10) Patent No.: US 9,072,770 B2
(45) Date of Patent: Jul. 7, 2015

(54) **AQUEOUS EXTRACTS OF *ANOECTOCHILUS* SPP. KINSENOSIDE AND PHARMACEUTICAL COMPOSITIONS USEFUL FOR HEPATOPROTECTION**

(75) Inventors: Wen-Chuan Lin, Taichung (TW); Jin-Bin Wu, Taichung (TW); Hui-Ya Ho, Taichung (TW); Wei-Lii Lin, Taichung (TW); Chang-Chi Hsieh, Taichung (TW); Hsin-Sheng Tsay, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 1141 days.

(21) Appl. No.: 12/966,714

(22) Filed: Dec. 13, 2010

(65) Prior Publication Data

US 2011/0142966 A1    Jun. 16, 2011

Related U.S. Application Data

(63) Continuation of application No. 11/898,563, filed on Sep. 13, 2007, now abandoned.

(30) Foreign Application Priority Data

Mar. 29, 2007  (TW) .............................. 96111007 A

(51) Int. Cl.
*A61K 31/7048* (2006.01)
*A61K 36/898* (2006.01)

(52) U.S. Cl.
CPC ........... *A61K 36/898* (2013.01); *A61K 31/7048* (2013.01)

(58) Field of Classification Search
None
See application file for complete search history.

(56) References Cited

U.S. PATENT DOCUMENTS 7,033,617 B2    4/2006  Shyur et al.

FOREIGN PATENT DOCUMENTS

| JP | 6293655 | 10/1994 |
| JP | 7076522 | 3/1995 |
| JP | 10056875 A | 3/1998 |

OTHER PUBLICATIONS

Huang et al. "Effects of tissue-cultured *Anoectochilus formosanus* Hay. extracts on the arachidonate metabolism". Bot. Bull. Academia Sinica (1991) 32; 113-119.*
Du et al. Hepatoprotective and Antihyperliposis Activities of in vitrol Cultured *Anoectochilus formosanus*, 2003, Phytotherapy Research, 17: 30-33.*
Huang et al., "Effects of tissue-cultured *Anoectochilus formosanus* Hay. extract on the arachidonate metabolism", 1991, Bot Bull Academia Sinica, 32: 113-119.
Zhang et al., "A Novel Total Synthesis of Kinsenoside and Gooderoside A relying on the efficient reaction of the chiral 2(5H)-furanones", 2005, J Asain Natural Prod Research, 7: 711-721.
Shih, CC et al., "Ameliorative effects of *Anoectochilus formosanus* extract on osteopenia in ovariectomized rats", J Ethnopharmacol, 2001, 77: 233-228.
Shih, CC et al., "Antihyperglycaemic and Anti-Oxidant Properties of *Anoectochilus formosanus* in Diabetic Rats", Clin Exp Pharmacol Physiol, 2002, 29: 684-688.
Cheng, Hy et al., "*Anoectochilus formosanus* Attenuates Amnesia Induced by Scopolamine in Rats ", J Chin Med, 2003, 14: 235-245.
Shih, CC et al., "Scavenging of Reactive Oxygen Species and Inhibition of the Oxidation of low Density lipoprotein by the Aqueous Extraction of *Anoectochilus formosanus*", Am J Chin Med, 2003, 31: 25-36.
Lin, JM et al., "Evaluation of the Anti-inflammatory and liver-protective Effects of *Anoectochilus formosanus, Ganoderma lucidum* and *Gynostemma pentaphyllum* in Rats", Am J Chin Med 1993 11: 59-69.
Lin, CC et al., "Antioxidant and Hepatoprotective Effects of *Anoectochilus formosanus* and *Gynostemma pentaphyllum*", Am J Chin Med, 2000 28: 87-96.
Du, XM et al., "Hepatoprotective and Antihyperliposis Activities of in vitro Cultured *Anoectochilus formosanus*", Phytother Res, 2003 17: 30-33.
Shih, CC et al., "Effect of *Anoectochilus foenosaanus* on FIBROSIS and Regeneration of the liver in Rats", Clin Exp Pharmacol Physiol, 2004, 31: 620-625.
Shih, CC et al., "Aqueous Extract of *Anoectochilus formosanus* Attenuate Hepatic Fibrosis Induced by Carbon Tetrachloride in Rats", Phytomedicine 2005 12: 453-460.
Shiau, YJ et al., "Conservation of *Anoectochilus formosanus* Hayata by artificial cross-pollination and in vitro culture of seeds", Bot Bull Acad Sin, 2002, 43: 123-130.
"Higher yielding Isolation of Kinsenoside in *Anoectochilus* and its Anti-hyperliposis effect", 2001 Pharmaceutical Society of Japan, 65-69.
Zhang, X et al., "Novel Total Synthesis of Kinsenoside", Chinese Journal of Synthetic Chemistry, 2004,12,317-318.
Ito, A et al., "Aliphatic and Aromatic Glucosides from *Anoectochilus koshunensis*", Phytochemistry, 1993,33: 1133-1137.
Du, XM et al., "Butanoic Acid Glucoside Compostion of Whole Body and in Vitro Plantlets of *Anoectochilus formosanus*", Phytochemistry, 1998,49: 1925-1928.
Wu, JB et al., "Hepatoprotective Activity of Kinsenoside from *Anoectochilus formosanus*", Wily Interscience-Phytotherapy Research, 2006, pp. 4.

* cited by examiner

*Primary Examiner* — Terry A McKelvey
*Assistant Examiner* — Catheryne Chen
(74) *Attorney, Agent, or Firm* — Ping Wang; Andrews Kurth LLP

(57) ABSTRACT

A pharmaceutical composition useful for hepatoprotection is provided. The composition comprises an effective amount of kinsenoside or a pharmaceutically acceptable salt or ester thereof. An aqueous extract of *Anoectochilus* spp. is also provided. The extract is substantially free of ethyl acetate-philic components.

4 Claims, 2 Drawing Sheets

AQUEOUS EXTRACTS OF *ANOECTOCHILUS* SPP. KINSENOSIDE AND PHARMACEUTICAL COMPOSITIONS USEFUL FOR HEPATOPROTECTION

This application is a continuation application of U.S. application Ser. No. 11/898,563, filed on Sep. 13, 2007, which claims priority from Taiwan Application No. 096111007, filed on Mar. 29, 2007. The entirety of all of the aforementioned applications is incorporated herein by reference.

FIELD

The present invention relates to a pharmaceutical composition comprising kinsenoside, which is useful in hepatoprotection. This invention also relates to an aqueous extract of *Anoectochilus* spp.

BACKGROUND

*Anoectochilus* spp. belong to Orchidaceae, wherein *Anoectochilus formosanus* Hayata is regarded as "the king of medicines" by the Taiwanese because of its diverse pharmacological effects, such as reducing blood pressure and blood sugar levels, hepatoprotection, and enhancing immunity. Therefore, *Anoectochilus formosanus* Hayata has generally been used as a folk medicine for treating liver fibrosis, diabetes and cardiovascular diseases.

The crude extracts of *Anoectochilus formosanus* Hayata have several pharmacological effects, such as antiosteoporosis (Shih C C et al., J Ethnopharmacol, 2001, 77: 233-228), antihyperglycemic effect (Shih C C et al., Clin Exp Pharmacol Physiol, 2002, 29: 684-688.; JP7076522), lipid-lowering effect (JP 6293655), improving memory and learning (Cheng H Y et al., J Chin Med, 2003, 14: 235-245.), inhibiting the oxidation of LDL (Shih C C et al., Am J Chin Med, 2003, 31: 25-36.), and treating tumors (U.S. Pat. No. 7,033,617). In addition, Lin et al. showed that *Anoectochilus formosanus* Hayata has hepatoprotective effects on carbon tetrachloride ($CCl_4$)—or acetaminophen-induced acute hepatitis (Lin J M et al., Am J Chin Med, 1993, 11: 59-69; Lin C C et al., Am J Chin Med, 2000, 28: 87-96). Du et al. also showed that aqueous extracts of *Anoectochilus formosanus* Hayata inhibited cell damage induced by $CCl_4$ in primary cultured rat hepatocytes (Du X M et al., Phytother Res, 2003, 17: 30-33). Recently, it was also shown that an aqueous extract of *Anoectochilus formosanus* Hayata attenuated hepatic fibrosis induced by both $CCl_4$ and dimethylnitrosamine in rats (Shih C C et al., Clin Exp Pharmacol Physiol, 2004, 31: 620-625; Shih C C et al., Phytomedicine, 2005, 12: 453-460).

Thus, the research has shown that *Anoectochilus formosanus* Hayata has an hepatoprotective effect. Since this herb is highly regarded in the Taiwanese herb market and cannot be colonal propagated quickly enough to sustain its uses, its prevalence in nature has depleted substantially. Although the vegetative propagation of *Anoectochilus formosanus* Hayata using tissue culture and modified cultivation of *Anoectochilus* spp. root have been achieved (Shiau Y J et al., Bot Bull Acad Sin, 2002, 43: 123-130; JP10056875(A)), only limited amounts of *Anoectochilus* spp. can be produced. Therefore, if the hepatoprotective compound(s) in *Anoectochilus formosanus* is(are) identified, the hepatoprotective preparations containing the compound(s) will be provided via synthesized and large-scale production.

The purpose of the present invention is to identify the major active compounds from *Anoectochilus formosanus* Hayata from both in vivo and in vitro experiments. Additionally, a fraction from *Anoectochilus formosanus* Hayata adverse to liver is also identified.

SUMMARY

In one aspect, the present invention provides a pharmaceutical composition useful for hepatoprotection, which comprises an effective amount of a compound of formula (I):

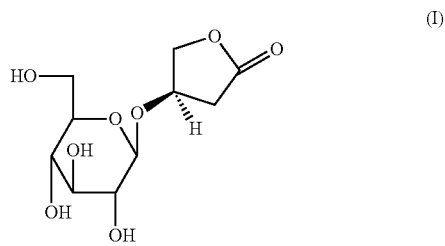

(I)

or a pharmaceutically acceptable salt or ester thereof, wherein the compound of formula (I) is kinsenoside.

In another aspect, the present invention provides extracts of *Anoectochilus* spp. that are substantially free of ethyl acetate-philic components.

In further aspect, the present invention provides uses of the compound of formula (I) or a pharmaceutically acceptable salt or ester thereof or the said extracts of *Anoectochilus* spp. for the manufacture of a pharmaceutical preparation for hepatoprotection.

DESCRIPTION

Figure 1:
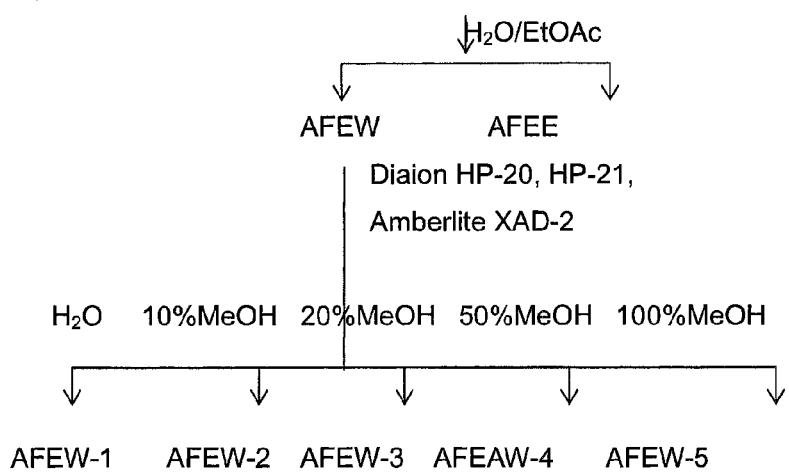
FIG. 1 shows a scheme illustrating the preparation of extracts of *Anoectochilus formosanus* Hayata.

The following describes the techniques and preferred embodiments in detail to enable those having ordinary skill in the art to realize the characteristics of the invention.

The term "ethyl acetate-philic components" as used herein refers to the components soluble in water and can be removed by partitioning with ethyl acetate.

The term "AFE" as used herein refers to the aqueous extracts of *Anoectochilus formosanus* Hayata.

The term "AFEW" as used herein refers to the water-soluble portion of the aqueous extract of *Anoectochilus formosanus* Hayata from which the ethyl acetate-soluble portion is removed, i.e. the water-soluble portion substantially free of ethyl acetate-philic components.

The term "AFEE" as used herein refers to an ethyl acetate-philic fraction of the extracts of *Anoectochilus formosanus* Hayata, i.e. an ethyl acetate portion obtained from partitioning the crude aqueous extracts of *Anoectochilus formosanus* Hayata with ethyl acetate.

The terms "fraction AFEW-1", "fraction AFEW-2", "fraction AFEW-3", "fraction AFEW-4", and "fraction AFEW-5"

as used herein refer to five fractions obtained from an AFEW subjected to a Diaion HP-20 column and respectively eluted with $H_2O$, 10% methanol in water, 20% methanol in water, 50% methanol in water, and 100% methanol.

This invention relates to both a pharmaceutical composition comprising a kinsenoside useful for hepatoprotection and an extract of *Anoectochilus* spp. that is substantially free of ethyl acetate-philic components. The invention also relates to uses of the pharmaceutical composition and the extract in the manufacturing of a pharmaceutical preparation.

It is known that the compound kinsenoside has a structure of formula (I):

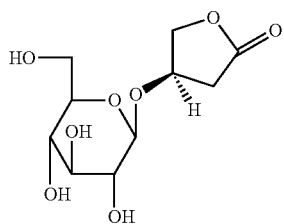

The inventors of the present invention found that the compound of formula (I) identified in *Anoectochilus formosanus* Hayata is one major component with a hepatoprotective effect. Specifically, those skilled in the art know that $CCl_4$ may cause hepatocellular damage and induce hepatitis in mice; however, the inventors of the present invention found that different extract fractions of *Anoectochilus formosanus* Hayata can reduce hepatocellular damage of $CCl_4$-induced hepatitis in mice, especially in the fractions with a large amount of the compound of formula (I). On the other hand, the ethyl acetate-philic fraction of the extract of *Anoectochilus formosanus* Hayata enhances hepatocellular damage. Without being bound by theory, it is believed that the compound of formula (I) is a major component in rendering the *Anoectochilus formosanus* Hayata hepatoprotective effect.

One aspect of this invention therefore provides a pharmaceutical composition useful for hepatoprotection, which comprises an effective amount of compound of formula (I) or a pharmaceutically acceptable salt or ester thereof. Administration of the pharmaceutical composition can be carried out in the appropriate ways, including, but not limited to, oral, subcutaneous, and/or intravenous administration. The compound of formula (I) or a pharmaceutically acceptable salt or ester thereof may be administered either alone or in combination with one or more pharmaceutically acceptable adjuvants. Furthermore, the compound of formula (I) or a pharmaceutically acceptable salt or ester thereof can be used in veterinary and human medicine.

Accordingly, the pharmaceutical composition of this invention may be formulated into any appropriate form used in hapatoprotection. For the preparation of the pharmaceutical preparation used in oral administration, the compound of formula (I) or a pharmaceutically acceptable salt or ester thereof can be mixed with suitable additives, such as excipients, stabilizers, or inert diluents. The suitable forms for administration such as tablets, coated tablets, capsules, soft-capsules, microcapsules, or aqueous solution, are prepared using the conventional methods. Suitable excipients that are inert to the activity of the compound of formula (I), include, for example, gum Arabic, lactose, dextrose, or starch, especially corn starch. Additionally, tablets also can be prepared by dry or wet granulation. Examples of suitable oily excipients or solvents are vegetable and animal oils, including, but not limited to, olive oil, sunflower oil, or fish liver oil.

For the preparation of the pharmaceutical preparation used in subcutaneous or intravenous administrations, the compound of formula (I) or a pharmaceutically acceptable salt or ester thereof can be prepared into the solutions, suspensions, or emulsions and be optionally mixed with suitable additives (such as solubilizers, emulsifiers, or other adjuvants). Examples of suitable solvents include water, physiologic saline solution, alcohols (such as ethanol, propanol, or glycerol), sugar solutions (such as dextrose or mannose solution), or a combination thereof.

The pharmaceutical composition of this invention optionally contains appropriate amounts of other pharmaceutically acceptable adjuvant(s) such as surfactants, emulsifiers, solubilizers, and the like.

It should be noted that the desired hepatoprotective effect of the pharmaceutical composition according to this invention is caused by the presence of the compound of formula (I) or a pharmaceutically acceptable salt or ester thereof. The amounts thereof are not critical. The frequency of administrating the pharmaceutical composition of this invention, for example, once daily, multiple times daily, or once every few days, depends on the conditions of the subject. Generally, the pharmaceutical composition of this invention contains, as the compound of formula (I), from about 0.1 to about 10% by weight of the compound of formula (I) or a pharmaceutically acceptable salt or ester thereof, especially from about 1 to about 5% by weight.

The amount of the compound of formula (I) or a pharmaceutically acceptable salt or ester thereof provided to a patient will vary depending on the severity of the disease to be treated. Generally, the amount of said compound of formula (I) provided to the patient is about 20 mg to about 200 mg per day for an adult who weighs 60 kg, more preferably about 40 mg to about 180 mg and most preferably about 120 mg to about 150 mg. However, the amount may be several-fold or more than 10-fold increased when treating patients with acute conditions, such as acute hepatitis.

The compound of formula (I) provided in the pharmaceutical composition of this invention can be prepared from a natural source or synthetic procedure. Preferably, the compound of formula (I) is prepared from *Anoectochilus* spp., especially *Anoectochilus formosanus* Hayata. Therefore, the compound of formula (I) can be prepared from *Anoectochilus* spp. using any appropriate extraction and isolation methods. See, Ito A et al., Phytochemistry, 1993, 33: 1133-1137; Du X M et al., Phytochemistry, 1998, 49: 1925-1928, each of which is incorporated herein by reference in its entirety. Further, the compound with formula (I) also can be prepared by total synthesis (See Zhang X et al., Chinese Journal of Synthetic Chemistry, 2004, 12, 317-318, which is incorporated herein by reference in its entirety).

The pharmaceutical composition of this invention may further be optionally combined with other active ingredients such as a hepatoprotective agent, hepatorepair agent or prophylactic agent for hepatodamage, wherein the active ingredients do not interfere with the activity of the compound of formula (I).

The present invention also relates to the extracts of *Anoectochilus* spp. that are substantially free of ethyl acetate-philic components. As described above, the ethyl acetate-philic fraction of the extracts of *Anoectochilus* spp. enhances hepatocellular damage. It is believed that an aqueous extract of *Anoectochilus* spp. substantially free of ethyl acetate-philic components can effectively prevent potential damages caused by the treatment of extracts of *Anoectochilus* spp. in subjects.

Preferably, the extract of *Anoectochilus* spp. according to the present invention is an aqueous extract of *Anoectochilus* spp. substantially free of ethyl acetate-philic components. The aqueous extract of *Anoectochilus* spp. can be prepared as follows: (1) fresh whole plants of *Anoectochilus* spp. are extracted with water, (2) the filtrate is partitioned with ethyl acetate, and (3) the ethyl acetate-philic fraction is removed. If necessary, the filtrate is partitioned successively with ethyl acetate to possibly reduce the ethyl acetate-soluble components.

Advantageously, the extracts of *Anoectochilus* spp. according to the present invention are substantially free of ethyl acetate-soluble components that are adverse to liver function; the said extracts of *Anoectochilus* spp. are used as an antiosteoporosis agent, hypoglycemic agent, or hypolipidemic agent, and applied in the treatment of tumor, improving memory and learning, or inhibiting the oxidation of the low density lipoprotein, for instance. Accordingly, the extracts of *Anoectochilus* spp. preferably comprise the compound of formula (I) when they are used in the hepatoprotection.

Furthermore, the present invention relates to the use of said aqueous extracts of *Anoectochilus* spp. for the manufacturing of a pharmaceutical preparation for the treatment of osteoporosis, hyperglycemia, hyperlipidemia, and tumors, as well as the improvement of memory and learning, inhibiting the oxidation of low density lipoprotein, and hepatoprotection.

The following examples are offered to further illustrate this invention.

MATERIALS AND METHODS (A) Plant Material

*Anoectochilus formosanus* Hayata plants were purchased from Yu-Jung Farm (Pu-Li, Taiwan) where they are cultivated. The plants were identified by the Institute of Chinese Pharmaceutical Sciences, China Medical University, where a plant specimen has been deposited with accession number CMU AF 0609.

(B) Reagents (1) Hydroxyproline, p-dimethylaminobenzoaldehyde, polyvinylpyrrolidone and hydrogen peroxide were provided by Sigma Chemical Co. (St Louis, Mo., USA).

(2) Carbon tetrachloride was obtained from Shimakyu Pure Chemicals (Osaka, Japan).

(3) DMEM (Dulbecco's modified Eagle's medium) was purchased from Hyclone (Logan, Utah, USA).

(4) Penicillin, streptomycin, amphotericin B and fetal bovine serum were purchased from Gibco Laboratories (Grand Island, N.Y., USA).

(C) Extraction and Isolation (1) Fresh whole plants of *Anoectochilus formosanus* Hayata (10 kg) were extracted with water (100 L) and then filtrated to yield an aqueous extract of *Anoectochilus formosanus* Hayata (AFE). The AFE was then partitioned successively with ethyl acetate (25 mL×3). The ethyl acetate layers were combined to obtain an ethyl acetate fraction (AFEE). The water-soluble layers were combined to obtain a water-soluble portion (AFEW). Alternatively, AFE can be prepared by heating dried plants of *Anoectochilus formosanus* Hayata in water.

(2) Both the ethyl acetate fraction (AFEE) and water-soluble portion (AFEW) were evaporated under a reduced pressure, yielding 47.4 g of a greenish oily residue and 218.4 g of a red residue, respectively. A red residue of AFEW (210 g) was subjected to a Diaion HP-20 column (Nippon Ressui Co Japan) and eluted with $H_2O$, 10%, methanol in water, 20% methanol in water, 50% methanol in water, and 100% methanol to give five fractions (AFEW-1, AFEW-2, AFEW-3, AFEW-4, and AFEW-5). The dry weights of fractions AFEW-1 to AFEW-5 were 141.38 g, 22.06 g, 8.16 g, 9.21 g and 3.78 g, respectively.

A general outline of the above preparation is provided in FIG. 1.

(3) The AFEW-2 fraction (10 g) was purified further on a silica gel (Si 60 F245; Merck, Germany) with chloroform/ethanol (8:3~15:8 concentration gradient) as the mobile phase to give four fractions (Fraction 1 to Fraction 4). Fraction 4 (4.5 g) was applied to the preparative high performance liquid chromatography (HPLC) to yield a pure compound (4.1 g). The pure compound was identified as kinsenoside, i.e. the compound of formula (I).

The conditions used for preparative HPLC were as follows: pump: Shimadzu LC-8A (Kyoto, Japan); mobile phase: water; column: Mightysil ODS RP-18 Aqua column (i.d. 20 mm, 250 mm long; 5 μm particle size; Kanto Chemical Co., Tokyo, Japan).

Figure 2:
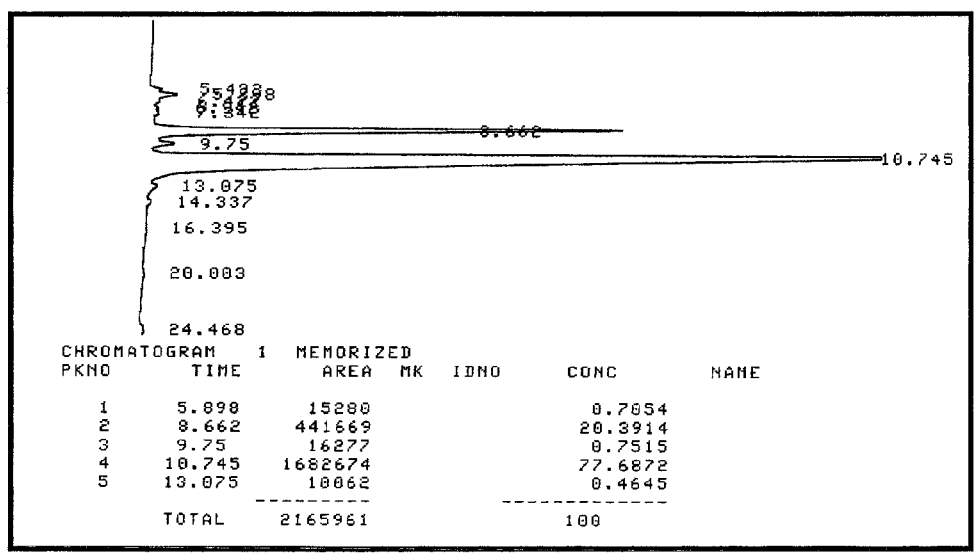
FIG. 2 shows the chromatographic profiles of Fraction 4 by using preparative high performance liquid chromatography (HPLC). The fraction AFEW-2 was purified further on a silica gel with chloroform/ethanol as the mobile phase to give four fractions (Fraction 1, Fraction 2, Fraction 3, and Fraction 4).
Figure 3:
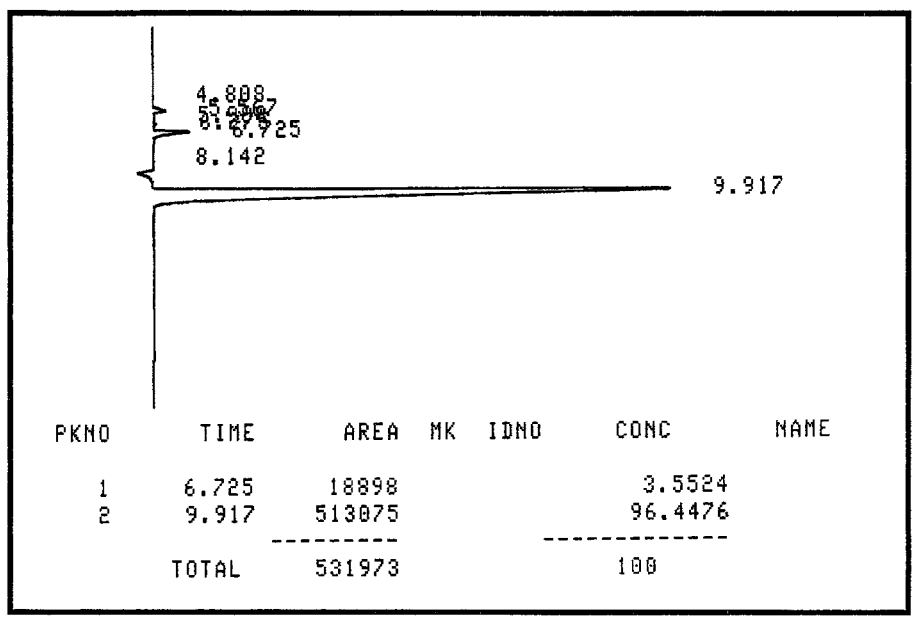
FIG. 3 shows a graph of mass spectroscopy of the major components of Fraction 4 in AFEW-2.

The chromatographic profile of Fraction 4 is shown in FIG. 2, wherein the Fraction 4 comprises 77.6% of major compound. The pure compound was identified by mass spectroscopy (Jeol GCmate, Tokyo, Japan) as shown in FIG. 3. Extensive NMR analysis ($^1H$, $^{13}C$, DEPT, COSY, HMQC, HMBC; Jeol 400 MHz, Tokyo, Japan) identified the major compound as kinsenoside:

3-(R)-3-β-D-glucopyranosyloxybutanolide, i.e. compound of formula (I).

Table 1 gives the complete NMR assignments of kinsenoside.

TABLE 1

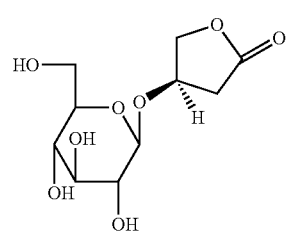

(I)

$^{13}C$ and $^1H$ NMR spectral data of kinsenoside (400 MHz, DMSO-$d_6$)

| C | | H | |
|---|---|---|---|
| 1 | 175.8 | 2 | 2.87 (dd, 17.8. 6.3) |
| 2 | 34.9 | — | 2.48 (dd, 17.9. 1.3) |
| 3 | 74.3 | 3 | 4.59 (dddd 6.0, 3.6, 2.2, 1.4) |
| 4 | 74.0 | 4 | 4.41 (dd, 10.2. 5.1) |
| | | | 4.38 (dd, 10.3. 1.8) |
| G-1 | 102.1 | G-1 | 4.24 (d, 7.8) |
| G-2 | 73.1 | G-2 | 2.92 (m) |
| G-3 | 76.9 | G-3 | 3.94 (m) |
| G-4 | 69.9 | G-4 | 3.04 (m) |
| G-5 | 76.5 | G-5 | 3.13 (m) |
| G-6 | 61.0 | G-6 | 3.44 (m) |
| | | | 3.66 (dd, 11.7. 5.8) |
| OH2 | | OH2 | 4.9 (d, 4.8) |
| OH3 | | OH3 | 5.0 (d, 5.1) |
| OH4 | | OH4 | 4.8 (d, 5.4) |
| OH6 | | OH6 | 4.5 (t, 5.8) |

(D) Determination of Kinsenoside Content

The kinsenoside contents in both the AFEW and AFEW-1 to AFEW-5 were determined by HPLC. The results indicated that the kinsenoside contents in AFEW, AFEW-2 and AFEW-3 fractions were approximately 18%, 82% and 35%, respectively. No kinsenoside was detected in fraction AFEW-1. Kinsenoside could be detected in fractions AFEW-4 and AFEW-5, but the content was very low.

Conditions used for HPLC were as follows: pump: Shimadzu LC-10ATvp; refractive index detector: Shimadzu RID-10A; column: Mightysil ODS RP-18 GP Aqua column (i.d. 4.6 mm, 250 mm long; 5 μm particle size); guard column: Mightysilk 4.6 mm×6 mm. The solvent system used was Milli-Q water at a flow rate of 0.5 mL/min.

Example 1

$CCl_4$-Induced Chronic Hepatitis in Mice

Male ICR mice were purchased from the National Laboratory Animal Center (Taipei, Taiwan) and were used for experiments when they reached 24 to 26 g body weight. Chronic hepatitis was induced in mice by oral administration of 0.1 mL of $CCl_4$ (diluted 1:19 in olive oil) per 10 g body weight twice a week for 3, 8 or 9 weeks. On the days of the $CCl_4$ treatment, the time interval between $CCl_4$ and drug administrations was 5 hours to avoid absorption interference. After the blood was drawn at the end of the experimental period, all mice were sacrificed at the same time and the liver and spleen were quickly removed and weighed after washing with cold normal saline and blotting dry. The largest lobe of liver was weighed and then completely dried at 100° C. for determination of the hydroxyproline content according to the method designed by Neuman and Logan (Neuman R E and Logan M A, *J Biol Chem*, 1950, 184: 299-306). Dried liver tissue (approx. 60 mg) was hydrolysed, then oxidized by $H_2O_2$, and reacted with p-dimethylaminobenzoaldehyde. The absorbance of the colored product was determined at 540 nm. The amount of hydroxyproline was expressed in μg/g wet tissue. The levels of plasma glutamate-pyruvate transaminase (GPT) and albumin were assayed spectrophotometrically (Cobas Mira Plus Chemistry Analyzer, Switzerland) using clinical test kits (Roche Diagnostics, Mannheim, Germany).

Experiment I

Chronic hepatitis was induced in mice by $CCl_4$ administration for 3 weeks. Since AFEE did not dissolve in water, it was suspended in polyvinylpyrrolidone (PVP). Therefore, the experiments were divided into two parts. For part I, mice were divided into three groups, those that received $CCl_4$ with $H_2O$, $CCl_4$ with AFE (2000 mg/kg) or $CCl_4$ with AFEW (1500 mg/kg) p.o. daily for 3 weeks. The control group received olive oil (vehicle for $CCl_4$) with $H_2O$. In part II, the mice were divided into two groups, those that received $CCl_4$ with PVP or $CCl_4$ with AFEE (500 mg/kg) p.o. daily for 3 weeks. The control group received the olive oil vehicle with PVP. After 1 week of $CCl_4$ treatment, blood was collected via the retro-orbital sinus of mice for serum GPT assays.

The results are shown in Table 2. $CCl_4$ treatment caused hepatocellular damage in mice, as indicated by an increase in plasma GPT activity after 1 and 3 weeks of $CCl_4$ administration. Mice that were treated daily with AFE (2000 mg/kg) or AFEW (1500 mg/kg) showed protection against $CCl_4$-induced hepatitis, with a reduced GPT level. In contrast, AFEE (500 mg/kg, daily) enhanced the increase in plasma GPT levels caused by $CCl_4$ administration for 1 and 3 weeks. These results clearly show that AFEW has a hepatoprotective action, while AFEE is adverse to liver function.

TABLE 2

Effects of AFE, AFEE and AFEW on the activities of serum GPT in $CCl_4$-treated mice after 1 and 3 weeks

| Drugs | Dose (mg/kg) | GPT (U/L) Week 1 | Week 3 |
|---|---|---|---|
| Olive oil + $H_2O$ | — | 40.3 ± 3.5 | 37.9 ± 2.0 |
| $CCl_4$ + $H_2O$ | — | 299.3 ± 15.9$^a$ | 1266.5 ± 162.0$^a$ |
| $CCl_4$ + AFE | 2000 | 160.5 ± 47.5$^c$ | 600.0 ± 142.7$^b$ |
| $CCl_4$ + AFEW | 1500 | 195.5 ± 29.7$^c$ | 306.0 ± 22.6$^c$ |
| Olive oil + PVP | — | 39.1 ± 2.9 | 37.5 ± 1.8 |
| $CCl_4$ + PVP | | 170.7 ± 17.4$^d$ | 740.0 ± 120.2$^d$ |
| $CCl_4$ + AFEE | 500 | 492.6 ± 103.6$^e$ | 1398.0 ± 268.6$^e$ |

All values are mean ± SE (n = 8).
$^a$p < 0.001 compared with olive oil + $H_2O$ group.
$^b$p < 0.05,
$^c$p < 0.01 compared with $CCl_4$ + $H_2O$ group.
$^d$p < 0.001 compared with olive oil + PVP group.
$^e$p < 0.05 compared with $CCl_4$ + PVP group.

Experiment II

Chronic hepatitis was induced in ICR mice by $CCl_4$ administration for 8 weeks. Since AFEW-4 did not dissolve in water, it was suspended in PVP. The experiment was divided into two parts. In part I, mice were divided into six groups, those that received $CCl_4$ with $H_2O$, $CCl_4$ with AFEW (1500 mg/kg), $CCl_4$ with AFEW-1 (1055 mg/kg), $CCl_4$ with AFEW-2 (130 mg/kg), $CCl_4$ with AFEW-3 (50 mg/kg) or $CCl_4$ with AFEW 5 (190 mg/kg) p.o. daily for 8 weeks. The control group received the olive oil vehicle with $H_2O$. In part II, mice were divided into two groups those that received $CCl_4$ with PVP or those that received $CCl_4$ with AFEW-4 (75 mg/kg) p.o. daily for 8 weeks. The control group received the olive oil vehicle with PVP.

An animal model of chronic hepatitis induced in mice by oral administration of $CCl_4$ twice a week for 8 weeks was used to investigate the hepatoprotective effect of AFEW-1 to AFEW-5. The result is shown in Table 4. Compared to the control group in week 8, the $CCl_4$-treated group had a markedly increased GPT activity, spleen weight and liver hydroxyproline level, and a decreased plasma albumin level. AFEW and AFEW-2 (a subfraction of AFEW) both reduced plasma GPT activity, spleen weight and liver hydroxyproline level in mice, and diminished the hypoalbuminemia. AFEW-1 reduced plasma GPT activity and liver hydroxyproline level in mice. AFEW-5 only reduced plasma GPT level in mice. According to these results, the subtraction of AFEW in which AFEW-2 was the most hepatoprotective fraction, while AFEW-1 only showed partial hepatoprotective action. AFEW-5 showed effects on the plasma GPT activity; however, there was no effect on improving liver fibrosis (hydroxyproline content is an indicator of liver fibrosis).

TABLE 4

Effect of AFEW and AFEW-1 to AFEW-5 on the levels of plasma GPT and albumin, spleen weight and contents of hepatic hydroxyproline in $CCl_4$-treated mice after 8 weeks

| Drugs | Dose (mg/kg/day) | Plasma GPT (U/L) | Plasma albumin (g/dL) | Spleen weight (g) | Liver hydroxyproline (μg/g tissue) |
|---|---|---|---|---|---|
| Olive oil + $H_2O$ | — | 36.4 ± 4.0 | 3.5 ± 0.1 | 0.18 ± 0.01 | 504.0 ± 26.6 |
| $CCl_4$ + $H_2O$ | — | 436.9 ± 62.5[b] | 2.9 ± 0.1[b] | 0.21 ± 0.03[a] | 1062.0 ± 189.5[b] |
| $CCl_4$ + AFEW | 1500 | 343.0 ± 19.0[c] | 3.4 ± 0.1[d] | 0.15 ± 0.01[c] | 698.0 ± 51.3[c] |
| $CCl_4$ + AFEW-1 | 1055 | 177.8 ± 20.0[e] | 3.1 ± 0.1 | 0.18 ± 0.01 | 660.1 ± 61.7[c] |
| $CCl_4$ + AFEW-2 | 130 | 246.9 ± 32.8[d] | 3.4 ± 0.0[d] | 0.15 ± 0.02[c] | 598.8 ± 39.1[d] |
| $CCl_4$ + AFEW-3 | 50 | 353.8 ± 20.4 | 3.2 ± 0.2 | 0.16 ± 0.01 | 845.2 ± 110.7 |
| $CCl_4$ + AFEW-5 | 190 | 258.6 ± 23.8[d] | 3.3 ± 0.3 | 0.20 ± 0.02 | 858.5 ± 54.0 |
| Olive oil + PVP | — | 38.3 ± 3.3 | 3.4 ± 0.2 | 0.18 ± 0.02 | 499.6 ± 27.6 |
| $CCl_4$ + PVP | — | 388.7 ± 59.0[e] | 2.8 ± 0.1[e] | 0.22 ± 0.02[e] | 1029.0 ± 170.6[e] |
| $CCl_4$ + AFEW-4 | 75 | 603.3 ± 192.9 | 3.2 ± 0.1 | 0.17 ± 0.03 | 898.0 ± 98.6 |

All values are mean ± SE (n = 10).
[a] $p < 0.01$,
[b] $p < 0.001$ compared with olive oil + $H_2O$ group.
[c] $p < 0.05$,
[d] $p < 0.01$ compared with $CCl_4$ + $H_2O$ group.
[e] $p < 0.001$ compared with olive oil + PVP group.

Experiment III

Male BALB/c mice were purchased from the National Laboratory Animal Center (Taipei, Taiwan) and were used for experiments when they reached approximately 22 g body weight. Chronic hepatitis was induced in mice by oral administration of 0.1 mL of $CCl_4$ (diluted 1:19 in olive oil) per 10 g body weight twice a week for 9 weeks. The experiment was divided into two parts. In part I, mice were divided into three groups, those that received $CCl_4$ with $H_2O$, $CCl_4$ with AFEW-1 (300 mg/kg), or $CCl_4$ with AFEW-1 (600 mg/kg) p.o. daily for 9 weeks. The control group received the olive oil vehicle with $H_2O$. In part II, the mice were divided into three groups, those that received $CCl_4$ with $H_2O$, $CCl_4$ with AFEW-2 (75 mg/kg), or $CCl_4$ with AFEW-2 (150 mg/kg) p.o. daily for 9 weeks. The control group received the olive oil vehicle with $H_2O$.

After 3 and 9 weeks of $CCl_4$ treatment, blood was collected via the retro-orbital sinus of the mice for serum GPT assays. The results are shown in Table 5. $CCl_4$ treatment caused hepatocellular damage in mice, as indicated by a marked increase in plasma GPT activity after 3 and 9 weeks of $CCl_4$ administration. According to these results, mice treated with AFEW-1 (600 mg/kg) and AFEW-2 (150 mg/kg) showed hepatoprotective action against chronic hepatitis induced by $CCl_4$, as the plasma GPT levels were significantly reduced in mice.

TABLE 5

Effect of AFEW-1 and AFEW-2 on the activities of serum GPT in $CCl_4$-treated BALB/c mice at 3 and 9 weeks

| | | GPT (U/L) | |
|---|---|---|---|
| Drugs | Dose (mg/kg) | Week 3 | Week 9 |
| Olive oil + $H_2O$ | — | 35.9 ± 3.8 | 33.4 ± 10.7 |
| $CCl_4$ + $H_2O$ | — | 1471.7 ± 408.2[a] | 2578.3 ± 874.1[a] |
| $CCl_4$ + AFEW-1 | 300 | 1126.7 ± 310.8 | 2097.0 ± 745.3 |
| $CCl_4$ + AFEW-1 | 600 | 838.3 ± 220.4[b] | 1552.0 ± 707.3[b] |
| Olive oil + $H_2O$ | — | 36.7 ± 1.1 | 35.6 ± 2.1 |
| $CCl_4$ + $H_2O$ | — | 1577.1 ± 114.0[a] | 1984.2 ± 224.9[a] |
| $CCl_4$ + AFEW-2 | 75 | 1329.1 ± 4480.0 | 1354.3 ± 669.8 |
| $CCl_4$ + AFEW-2 | 150 | 1120.0 ± 185.1[b] | 1018.5 ± 354.0[b] |

All values are mean ± SE (n = 10).
[a] $p < 0.001$,
[b] $p < 0.05$,
[c] $p < 0.01$,
[d] $p < 0.001$ compared with $CCl_4$ + $H_2O$ group.

Example 2

Cell Culture and Hydrogen Peroxide Cytotoxicity Assay

BALB/c normal liver (BNL) cells were purchased from Bioresources Collection and Research Center (Hsinchu, Taiwan). Cell lines were grown in DMEM (Dulbecco's modified Eagle's medium) with 50 IU/mL penicillin, 50 μg/mL streptomycin, 50 IU/mL amphotericin B and 10% fetal bovine serum. For cytotoxicity assays, cells ($5 \times 10^3$ cells/well) were plated into 96-well culture plates and allowed to attach overnight. The medium was replaced with fresh medium (as control) or with various concentrations of AFEW, AFEW-1 or kinsenoside for 16 hours. The cells were then washed with PBS and further treated with various doses of hydrogen peroxide (0.125-4.00 μM) for 2 hours. After $H_2O_2$ cytotoxic treatment, the percentage of viable cells was determined using a CellTiter 96 Aqueous Non-Radioactive Cell Proliferation Assay kit (Promega, Madison, Wis., USA). Reagent solution (20 μt) was added to each well and incubated at 37° C. in humidified 5% $CO_2$ for 1 hour. Then, the absorbance was measured at 490 nm using a 96-well plate reader (Multiskan Spectrum, Labsystem, Thermo Electron Corporation, Finland).

In Vitro Experiment and Results

In the in vitro experiment, a pure kinsenoside was used to replace AFEW-2. The hepatoprotective effect of AFEW, AFEW-1 and kinsenoside on the injury induced by $H_2O_2$ in BNL was shown in Table 6. The $LD_{50}$ concentrations of $H_2O_2$ were markedly increased in BNL cells by pretreatment with AFEW (100 and 200 μg/mL) or kinsenoside (20 and 40 μg/mL), but not by AFEW-1 (75 and 150 μg/mL), indicating that the hepatoprotective effect of AFEW is mostly due to kinsenoside, the major compound of AFEW-2.

TABLE 6

Effect of pretreatment with AFEW, AFEW-1 and kinsenoside on the $LD_{50}$ of $H_2O_2$-induced BNL cell death

| Drug | Concentration (μg/mL) | $H_2O_2$ $LD_{50}$(μM) (95% confidence limits) |
|---|---|---|
| Control | — | 0.69 (0.64-0.76) |
| AFEW | 100 | 0.81 (0.75-0.87)[a] |
| AFEW | 200 | 1.05 (0.96-1.14)[a] |
| AFEW-1 | 75 | 0.62 (0.58-0.66) |
| AFEW-1 | 150 | 0.62 (0.57-0.67) |
| Kinsenoside | 20 | 0.81 (0.74-0.88)[a] |
| Kinsenoside | 40 | 1.17 (1.01-1.36)[a] |

Data represent the means of triplicate determination from three experiments.
[a]Significance of difference compared with control.

Statistical Analyses

Data from in vivo experiments were treated by one-way analysis of variance and Dunnett's test was applied. The significance level was set at p☐00.05. The $LD_{50}$ values and 95% confidence limits for $H_2O_2$-induced BNL cell death were calculated according to the method of Litchfield and Wilcoxon (Litchfield J T, Wilcoxon F. 1949. A simplified method of evaluating dose-effect experiments. *J Pharmaeol Exp Ther* 96: 99-113). The significance of differences between the $LD_{50}$ values was also tested using this method.

The above examples are offered to illustrate the principle and effects of the present invention, and are not intended to limit the invention in any manner. Indeed, various modifications of the invention in addition to those described herein will become apparent to those skilled in the art from the foregoing description and the accompanying figures without departing from the spirit of the invention. Such modifications are intended to fall within the scope of the appended claims.

What is claimed is:

1. A method for treating hepatitis in an animal, comprising administering to the animal suffering from hepatitis an effective amount of a pharmaceutical composition comprising an extract from *Anoectochilus* spp., wherein the extract is produced by (1) extracting *Anoectochilus* spp. plant material with water to produce an aqueous extract, and (2) partitioning the aqueous extract successively with ethyl acetate and removing an ethyl acetate fraction after each partition to produce an ethyl acetate partitioned aqueous extract, which is substantially free of ethyl acetate-philic components.

2. The method according to claim 1, wherein the animal is a human being.

3. The method according to claim 1, wherein the *Anoectochilus* spp. is *Anoectochilus formosanus*.

4. The method according to claim 1, wherein in step (1), the aqueous extract is prepared by heating the *Anoectochilus* spp. plant material in water.

\* \* \* \* \*